(12) United States Patent
Furumoto

(10) Patent No.: US 6,228,075 B1
(45) Date of Patent: *May 8, 2001

(54) ALEXANDRITE LASER SYSTEM FOR HAIR REMOVAL

(75) Inventor: Horace W. Furumoto, Wellesley, MA (US)

(73) Assignee: Cynosure, Inc., Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/270,227

(22) Filed: Mar. 15, 1999

Related U.S. Application Data

(63) Continuation of application No. 09/161,871, filed on Sep. 28, 1998, now abandoned, which is a continuation-in-part of application No. 08/744,344, filed on Nov. 7, 1996, now Pat. No. 5,871,479.

(51) Int. Cl.[7] ..................................................... A61B 18/18
(52) U.S. Cl. .................................................................. 606/9
(58) Field of Search ........................... 606/9, 10, 13–17; 607/89

(56) References Cited

U.S. PATENT DOCUMENTS

| | | |
|---|---|---|
| 3,538,919 | 11/1970 | Meyer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |

(List continued on next page.)

FOREIGN PATENT DOCUMENTS

| | | |
|---|---|---|
| 0 142 671 A1 | 5/1985 | (EP) . |
| 0 458 576 A2 | 11/1991 | (EP) . |
| 0 575 274 A1 | 12/1993 | (EP) . |
| WO 91/18646 | 12/1991 | (WO) . |
| WO 95/15725 | 6/1995 | (WO) . |
| 95/335518 | 12/1995 | (WO) . |

OTHER PUBLICATIONS

Finkelstein, L. H., "Epilation of Hair–Bearing Urethral Grafts Utilizing the Neodymium: YAG Surgical Laser," *Lasers in Surgery and Medicine* 10:189–193 (1990).

Goldman, M. P., "Sclerotherapy—Treatment of Varicose and Telangiectatic Leg Veins," *Second Edition, Mosby*, pp. 454–467 (No Date Given).

"Temperature Indicating Tab, Crayons, Lacquers, and Pellets," pp. F5–F6, F13, F19 (Advertisement Brochure—No Date Given).

"Hydrogel Dressings Contain Particles During Laser Therapy," *Dermatology Times 94–01*, ISSN–01966197, pp. 26 (1994).

(List continued on next page.)

*Primary Examiner*—Lee Cohen
*Assistant Examiner*—Roy Gibson
(74) *Attorney, Agent, or Firm*—Hamilton, Brook, Smith & Reynolds, PC

(57) ABSTRACT

A long pulse alexandrite laser hair removal system is disclosed using light pulses of greater than 1 msec and fluences between 10 and 50 $J/cm^2$. The use of an alexandrite laser allows good penetration while still achieving an acceptable combination of hemoglobin and melanin absorption. The use of an index-matching application on the skin sections to be treated is also described. This substance will be absorbed into the epidermal layer to provide better coupling of the laser light into the skin. Also, and most advantageously, it will reduce reflections at the epidermal-dermal junction, which can lead to the damage of the skin. Also a topical thermal or photochromic indicator is suggested since skin irradiation in the near-infrared generally does not produce any characteristic skin color change as is found when using pulsed dye lasers, for example.

2 Claims, 14 Drawing Sheets

U.S. PATENT DOCUMENTS

| | | |
|---|---|---|
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,813,412 | 3/1989 | Yamazaki et al. . |
| 4,829,262 | 5/1989 | Furumoto . |
| 5,059,192 | 10/1991 | Zaias . |
| 5,226,907 | 7/1993 | Tankovich . |
| 5,255,277 | 10/1993 | Carvalho . |
| 5,290,273 | 3/1994 | Tan . |
| 5,405,368 | 4/1995 | Eckhouse . |
| 5,423,800 | 6/1995 | Ren et al. . |
| 5,527,350 | 6/1996 | Grove et al. . |
| 5,558,667 | 9/1996 | Yarborough et al. . |
| 5,595,568 | 1/1997 | Anderson et al. . |
| 5,658,323 | 8/1997 | Miller . |
| 5,735,844 * | 4/1998 | Anderson et al. ................ 606/9 |
| 5,868,732 | 2/1999 | Waldman et al. . |
| 5,879,346 | 3/1999 | Waldman et al. . |
| 5,879,376 | 3/1999 | Miller . |
| 6,027,495 | 2/2000 | Miller . |

OTHER PUBLICATIONS

Dover, J. S., et al., "Pigmented Guinea Pig Skin Irradiated with Q–Switched Ruby Laser Pulses," pp. 43–49, *Arch Dermatol*, vol. 125 (Jan. 1989).

Polla, L., et al., "Melanosomes are a Primary Target of Q–Switched Ruby Laser Irradiation in Guinea Pig Skin," *The Journal of Investigative Dermatology*, vol. 89, No. 3, p. 281–285 (1987).

\* cited by examiner

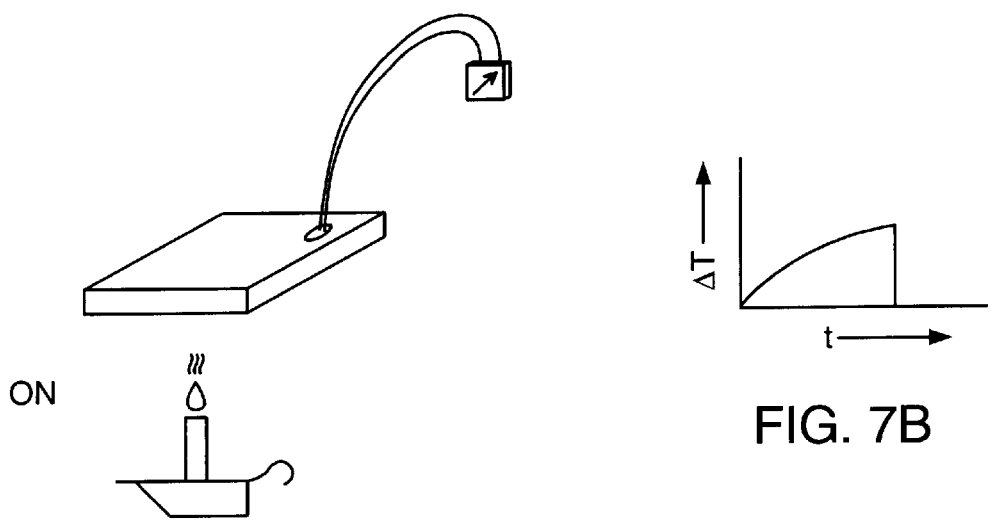
ON
FIG. 7A
FIG. 7B
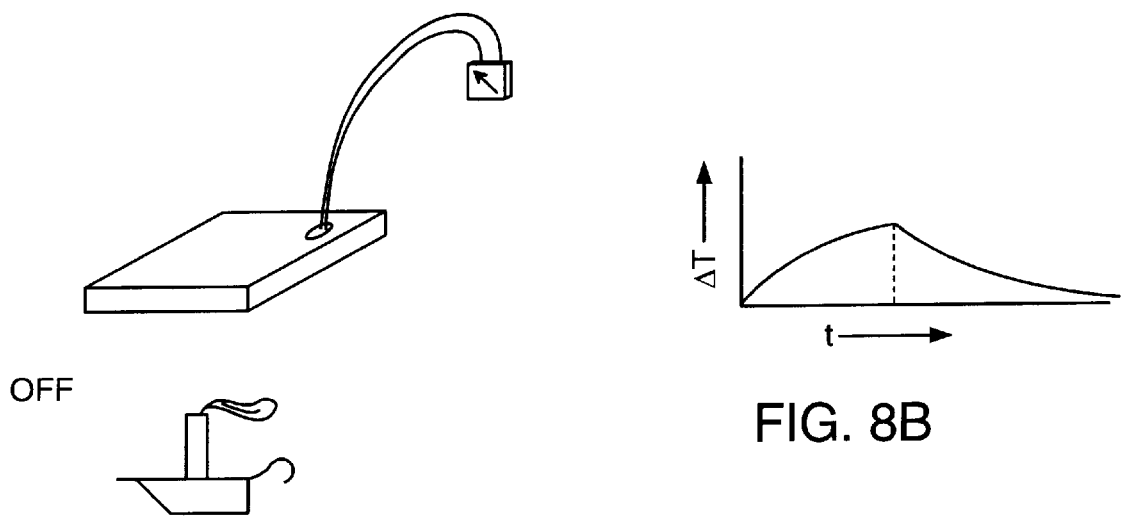
OFF
FIG. 8A
FIG. 8B $V(t) = I_o R(1-e^{-1/RC})$  (3a)

WITH $t \to \infty$
ASYMPTOTIC LIMIT
$V(t \to \infty) = I_o R$
SYSTEM DISCHARGE WHEN
$I_o = 0$ AT $t = t_0$ $V(t) = V(t_0)e^{-(t-t0)/RC}$ $V(t) = V_C(1-e)^{-1/RC}$  (3b)

WITH $t \to \infty$
$V(t \to \infty) = V_C$
SYSTEM DISCHARGES WHEN
$V_C$ IS SHORTED OUT AT $t = t_0$ $V(t) = V_C(t_0)e^{-(t-t0)/RC}$

ALEXANDRITE LASER SYSTEM FOR HAIR REMOVAL

RELATED APPLICATIONS

This application is a Continuation of U.S. patent application Ser. No. 09/161,871, filed Sep. 28, 1998, now abandoned, which is a Continuation-in-Part of U.S. patent application Ser. No. 08/744,344, filed Nov. 7, 1996, now U.S. Pat. No. 5,871,479, which is related to U.S. Ser. No. 08/745,133, filed Nov. 7, 1996, the teachings of which are incorporated herein by this reference in their entirety.

BACKGROUND OF THE INVENTION

Historically, there have been a number of options for the permanent removal of hair. Electrolysis has been the most commonly selected approach, in which an operator, usually a electrologist, attaches an electrode to each individual hair shaft, with the patient typically holding a second electrode. An electrical current is then passed through the hair shaft and the hair follicle through the papilla. This precisely directed current can induce permanent injury in the follicle and papilla, stopping the future production of the hair shaft.

Problems exist with the electrolysis technique, however. The success with which hair is permanently removed varies greatly from patient to patient. Moreover, the process is slow since each hair follicle must be individually treated, and there is some discomfort associated with the electric current.

The removal of hair using lasers is another approach that has found only limited success. Numerous techniques have been taught in the prior art. Each, however, suffers from drawbacks such as poor ultimate success in stopping hair growth even after multiple treatments, excessive injury to the tissue surrounding the hair follicles and papilla, and excessively large and expensive laser systems.

One approach relies on a pulsed laser source and the use of an exogenous absorber. A commercially available hair dye solution is first applied to the skin containing the unwanted hair and allowed to migrate along the hair shafts and into the follicles. The skin is then irradiated with a spot size of approximately 0.5 centimeters using a Q-switched YAG laser, or other short pulsed laser system. The pulse durations used by the lasers tend to be short, 15 nsec for the Q-switched laser. It appears that the sub-microsecond pulse durations shocks the hair follicle, which stops hair production, but only for a limited time. After months, the follicle again begins to produce hair, requiring further treatments or other techniques to yield any lasting success.

Other approaches have been proposed that rely on flashlamps, instead of lasers. This has the advantage of a less expensive, reasonably portable light source, but flashlamps create their own control problems. It is difficult to deliver light from the flashlamp to the skin, so that it must be placed in proximity to the skin. The reflectors that surround the flashlamp and collect the light and direct it to the skin must be precisely built and calibrated. Any error can cause hot spots in the spatial energy distribution. This can lead to under-treatment in some areas and burning in others. Moreover, the bandwidth of the light from these flashlamps is broad, usually including the visible and stretching into the longer infrared wavelengths. These longer wavelengths are well absorbed by water that occupies the skin. Thus, the light from these sources tends to penetrate very poorly, which leads to higher fluence levels to sufficiently treat deeper-lying hair producing structures with the concomitant risk of burning or damaging the skin.

Still other approaches use laser light delivery systems that inject light into only a single hair follicle at a time. These have the advantage of a reduced concern for damaging tissue between hair follicles but have many of the same disadvantages associated with the electrolysis. That is, each individual hair and hair follicle must be separately treated.

Long pulse ruby lasers have recently been used in hair removal. The high energy ruby lasers, however, are generally large, inefficient types of laser light generators, when very long pulses are generated.

SUMMARY OF THE INVENTION

The present invention is directed to a long pulse alexandrite laser hair removal system. The use of an alexandrite in the present invention allows operation in the near-infrared, specifically in a 100 nm range surrounding 760 mn, and ideally at approximately 755 nm and a surrounding 50 nm range. Infrared in this range allows good penetration while still achieving an acceptable ratio of hemoglobin to melanin absorption. Moreover, with use of a long pulse alexandrite laser, the effective pulse durations are now on the order of the thermal relaxation times of the targeted hair structures, which are about 28 msec, and longer than the relaxation times of the skin, which is about 12 msec.

In specific embodiments, it is desirable to use an index-matching application on the skin sections to be treated. This substance covers the epidermal layer to provide better coupling of the laser light into the skin.

The skin is preferably treated with laser pulses of greater than a millisecond, preferably approximately greater than 40 msec. Each pulse should contain a fluence of between 10 and 50 Joules per square centimeter ($J/cm^2$). During each treatment session, each treated section of the skin is preferably irradiated with one such pulse, although multiple pulses could be used. Even so, permanent and complete laser removal may require three to four repeat treatment sessions, with weeks to months long dwell times between each session.

For effective and quick treatment, spot sizes should be greater than 7 millimeters (mm). In the preferred embodiment, they are 10–12.5 mm and even up to 15 mm in diameter circles, at 10 $J/cm^2$ of fluence.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

DESCRIPTION OF THE DRAWINGS

FIG. 7A illustrates a slab of a good thermal conductor being heated;

FIG. 7B is a plot of the temperature versus time of the slab of FIG. 7A;

FIG. 8A illustrates the heated slab of FIG. 7A in a cooling state;

FIG. 8B is a plot of the temperature versus time of the slab of FIG. 8A;

DETAILED DESCRIPTION OF THE PREFERRED EMBODIMENT

Figure 1:
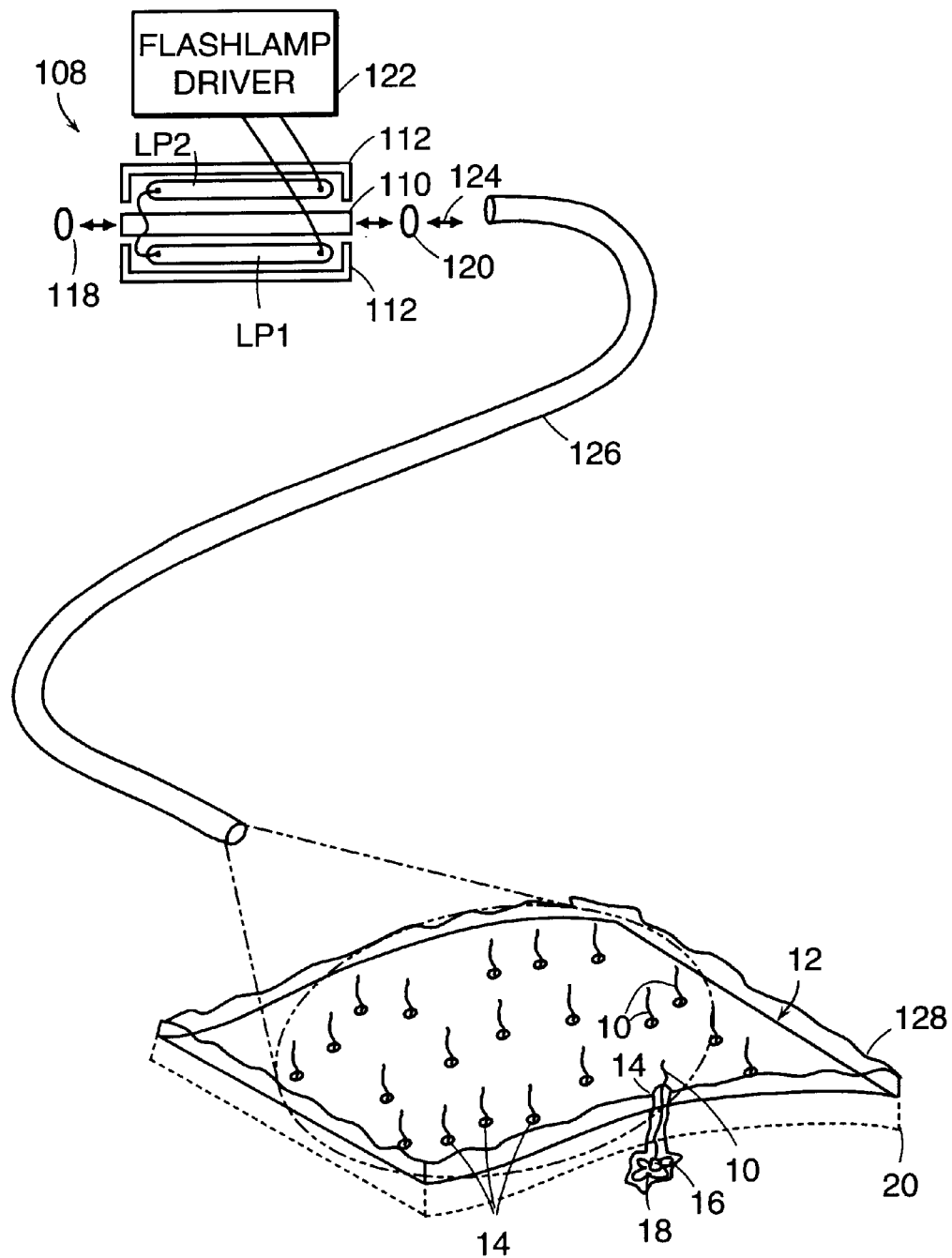
FIG. 1 is a schematic view of the inventive alexandrite laser system illustrating its use for the treatment of hair-bearing skin.

FIG. 1 shows an alexandrite laser system for hair removal, which has been constructed according to the principles of the present invention. An alexandrite laser 108 generally comprises one or more flashlamps LP1 and LP2 that are disposed around a usually centrally located alexandrite crystal gain medium 110. The flashlamps 114 directly irradiate the gain medium or via the associated reflector 112. The flashlamps LP1, LP2 are driven by a flashlamp driver 122.

The alexandrite crystal 110 generates a laser light output pulse 124 in the laser's resonant cavity, which is defined by mirrors 118 and 120. Mirror 120 is only partially reflecting and thus provides the laser's output aperture. The reflectance of the output aperture mirror 120, however, is relatively high. Generally, in Q-switched lasers, the reflectance of the output aperture mirror will be less than or equal to 50%. This is due to the fact that high peak pulse powers are to be generated, but only for a short pulse duration. In contrast, in the present long pulse alexandrite laser system, the driving factor is to increase the laser's efficiency when operating just above the laser's pumping threshold. As a result, the reflectance of mirror 120 in the present invention is preferably greater than or equal to 80%.

Another design factor is the length of the resonant cavity as defined by mirrors 118 and 120. In the preferred embodiment, the cavity is relatively short, 15 inches or approximately 45 centimeters. The mirrors 118 and 120 have large radii of curvature forming a near concentric resonant cavity. This configuration further decreases losses and increases efficiency, but beam divergence also increases.

The pulse from the cavity is preferably coupled into a medical delivery system 126, which can take any one of a number of different forms including fiber optics. In the illustrated example, it is a fiber optic light guide that transmits the pulse from the laser to the hair-bearing skin 12 that is to be treated. Specifically, a quartz fiber delivery system can be used. The longer pulses that are characteristic of the present invention allows the use of the quartz. Although relatively high energies are generated with the laser light output pulse 124, 20–40 J, the low peak powers avoid damage to the delivery system. In either case, the core diameter should be between 1 and 1.5 millimeters. This relatively large diameter accepts the high beam divergence created by the resonant cavity using lens with easily available focal lengths from 2 to 10 cm.

Figure 2A:
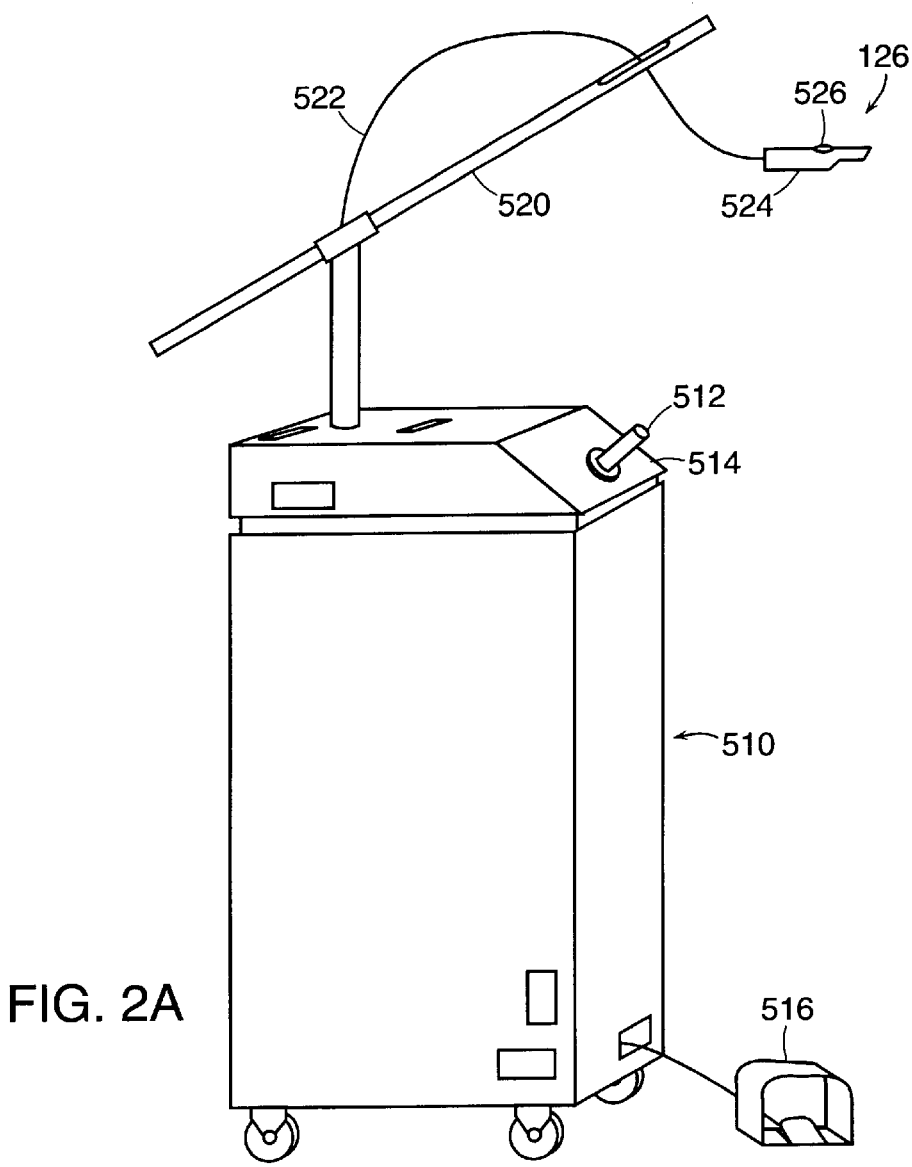
FIGS. 2A and 2B are schematic views of two embodiments of the alexandrite laser system.
Figure 2B:
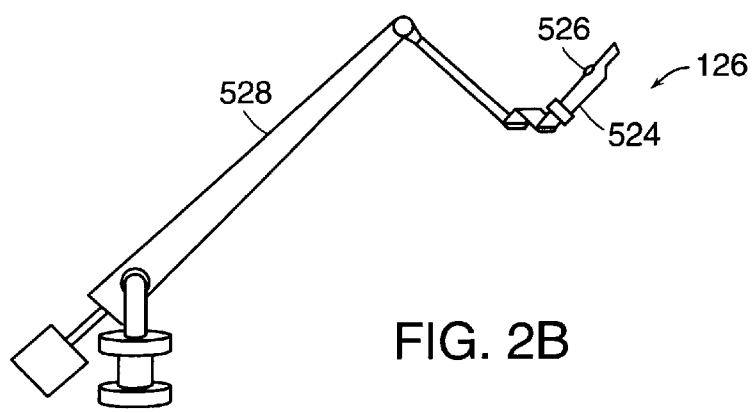

FIGS. 2A and 2B show two implementations of the laser system that would be appropriate for in-office treatment. It comprises a main unit 510 that has a calibration port 512 and a front control panel 514. A foot switch is provided for convenient control. A swing arm 120 holds the optical delivery fiber 522 that ends in a handpiece 524. The handpiece has a finger switch 526 also for activation. FIG. 2B shows another embodiment using an articulated arm 528 as in the delivery system 126. This embodiment is compatible with the quartz fiber delivery system.

A similar system is disclosed in related U.S. patent application Ser. No. 08/745,133, filed Nov. 7, 1996, entitled "Method For Treatment of Unwanted Veins and Device Therefor", by Horace W. Furumoto, et al., the teachings of which are incorporated herein by this reference in their entirety.

The use of the alexandrite laser is preferred to other laser systems for a number of reasons. Alexandrite is tunable through a 100 nm range surrounding 760 nm. This range has a number of advantages relative to ruby or pulsed dye lasers that have been used in the past.

Figure 3:
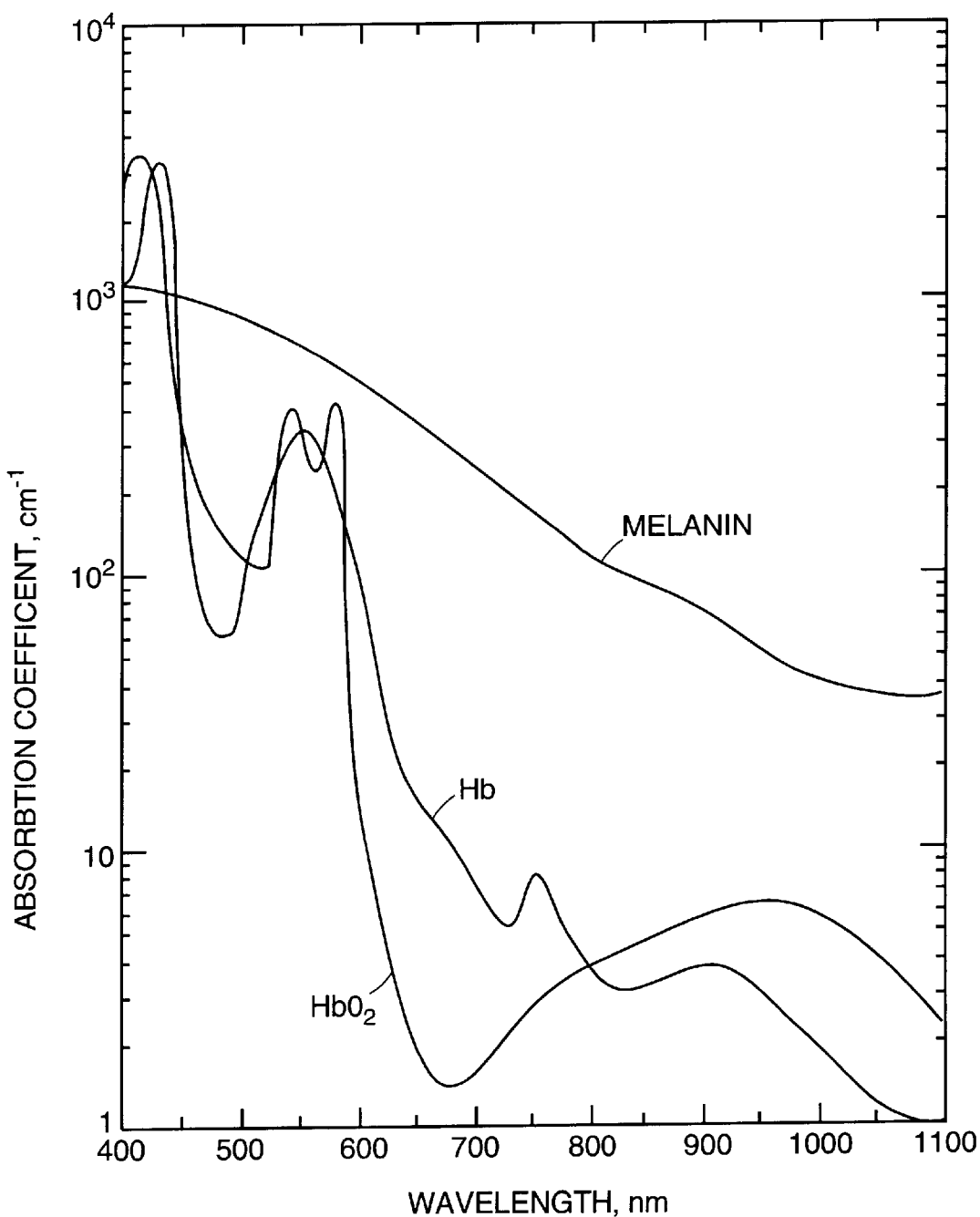
FIG. 3 is a plot of the spectral absorption of hemoglobin and melanin.

Pulsed dye lasers operating in the 577–585 nm range are well absorbed by the deoxy-hemoglobin (Hb) and oxy-hemoglobin (HbO₂) relative to the melanin, as shown in FIG. 3. This provides good selectivity. The problem, however, is that the total absorption of the melanin is very high. As a result, the laser light does not penetrate very deeply into the dermal layer. To effectively render inactive the hair-producing skin structures, the light must penetrate deeply, up to 5 millimeters, to the hair papilla and the nutrient blood vessels that surround it.

Ruby lasers operating at 694 nm do achieve good penetration since the absorption of melanin is incrementally lower at this wavelength. The problem here, however, is that the Hb and HbO₂ have low absorptions at this wavelength, as also shown in FIG. 3. To effectively and permanently stop the growth of a hair, the light must penetrate down to the papilla and be absorbed in the papilla but also the surrounding nutrient blood vessels. Ruby lasers do not achieve this destruction because of their poor blood absorption. This is why the prior art teaches the use of exogenous absorbers. These absorbers, however, do not solve the problem since they do not reach to the depth of the papilla.

In contrast, in the 50 nm range surrounding 755 nm, where the inventive alexandrite laser system operates, melanin absorption is lower, compared to the ruby laser. Thus, better penetration is achieved down to the hair's papilla to the approximately five millimeter depth. Somewhat more importantly, however, is the fact that the absorption of Hb peaks in this range and the absorption of $HbO_2$ is substantially higher than at the ruby laser's wavelength. These factors combine to allow laser light to 1) penetrate to the depth of the papilla and blood vessels supplying the papilla; and 2) then be absorbed by the melanin, and hemoglobin containing blood cells in those vessels. Because of the long pulse durations, blood in small vessels between the surface of the skin and the papilla diffuse its heat to surrounding tissue and is not heated to denaturation. Blood in the papilla is heated because the heat is confined within the papilla which is a large structure.

The use of the alexandrite laser has further, more utilitarian, advantages. Long pulse dye and ruby lasers tend to be larger, inefficient devices. Moreover, pulsed dye lasers have the added drawback of requiring the dye gain media, which are not efficient in the infrared. In contrast, long pulse alexandrite laser systems are substantially smaller, and the conversion of energy from the flashlamps into the output laser light pulse is much more efficient than either dye or ruby lasers.

A still further advantage relative to dye lasers is the fact that alexandrite lasers generally allow longer pulse durations than dye lasers. This factor is relevant because the pulse duration of the irradiating light is important for selectivity. If the pulse duration is too long, the heat absorbed by the papilla and surrounding vessels would diffuse into the surrounding dermal tissue so that the papilla and blood vessels would not be selectively heated to the degree necessary to destroy only those structures. If the pulse durations are too short, however, the smaller light absorbing chemical species, such as the blood hemoglobin or melanin, and smaller blood vessels will not be cooled by heat diffusion and the epidermis will be overheated and burn. This effect can cause purpura, bleeding, and burning but also generally is not effective at permanently stopping hair growth. This is why the shorter pulse duration ruby lasers only find limited success in permanently removing the hair.

In the preferred embodiment, the laser system 108 irradiates the treated skin section with laser light output pulses having durations of between 1 and 40 msec. The best results, however, have been achieved using pulses of approximately 5 to 10 msec or longer.

Use of the long pulse alexandrite laser 108 also has certain advantages relative to other alexandrite laser systems used in the prior art for tattoo removal and pigmented lesion treatment. Historically, alexandrite lasers generally have been viewed as difficult to implement. The Q-switching element in the laser cavity made operation of the laser unstable. In the present laser system 108, the Q-switching element is removed and the gain medium laser is driven into the longer pulse durations. This improves the operation of the laser.

The invention additionally, preferably includes the use one or more topical applications on the skin to be treated. Mineral oil, K-Y® jelly or any other wet, penetrating, biocompatable application is preferably applied in a layer 128 over the hair-bearing skin 12 that is to be then laser treated. The layer provides gross refractive index-matching.

In addition to the index-matching layer, a thermo- or photo-sensitive irradiation marker is included as a separate layer to the index-matching layer or in a common vehicle with the index-matching substance. This thermochromic or photochromic marker preferably changes color or state in response to being exposed by the laser light output pulse. This indicates to the operator those portions of the skin surface 12 that have been exposed. The marker may be a temperature indicating crayon or liquid that liquifies at a known temperature, such as sold commercially by Omega Engineering, Inc., although bio-compatibility has not yet been confirmed with these products.

The use of a thermochromic or a photochromic marker is useful when irradiating the skin with light in the near-infrared. When skin is exposed to pulsed light in the shorter frequencies, such as 577–585 nm, there is an instantaneous purpura effect which acts as a record of those portions of the skin that have been treated. This effect does not occur when the skin is irradiated with the near-infrared. Use of the marker which changes color or state, for example, in response to the light or indicated heat, however, provides the helpful indication of those portions of the skin that have been treated.

Figure 4:
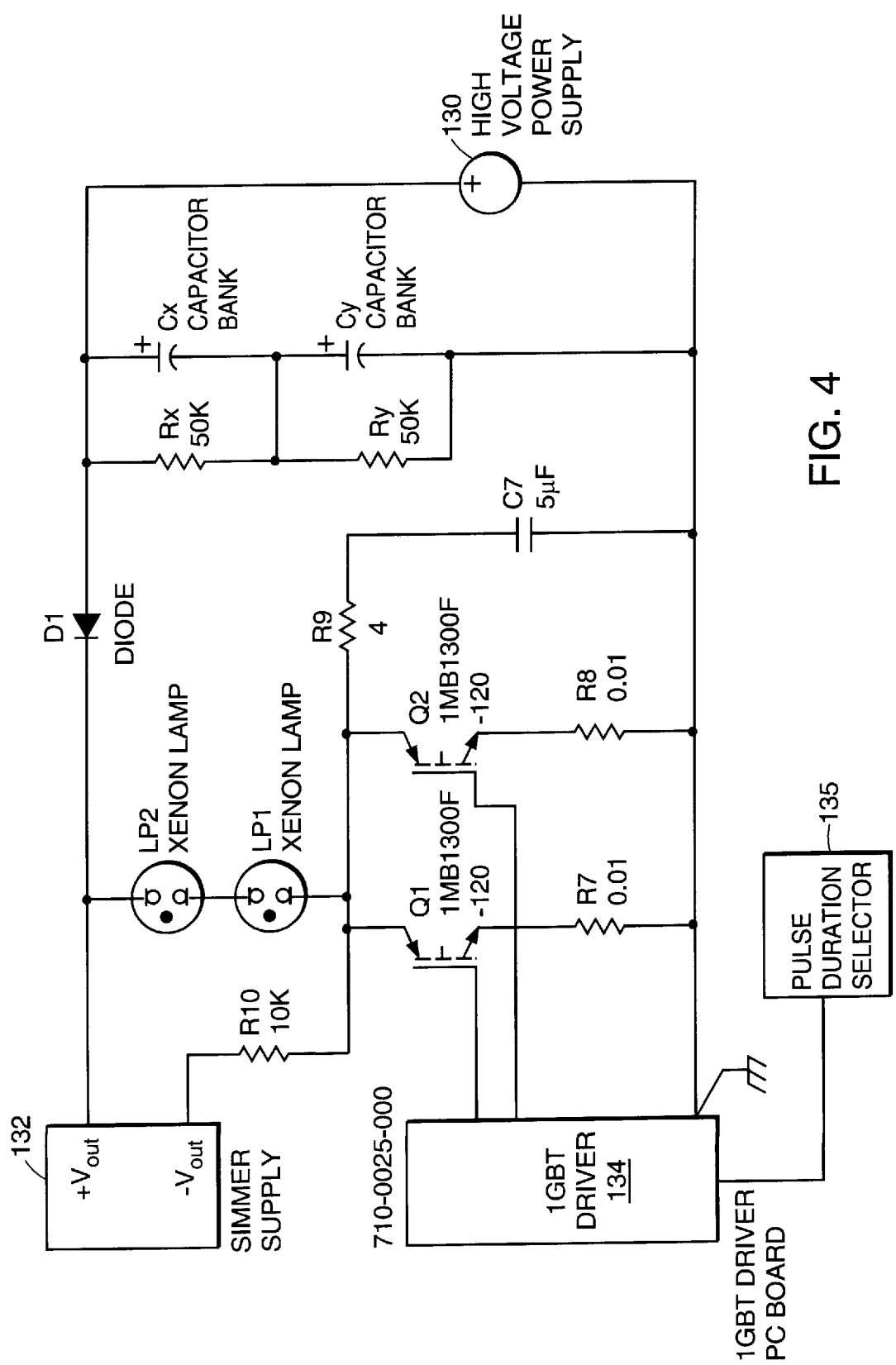
FIG. 4 is a circuit diagram showing an inventive flashlamp driver for the laser system.

FIG. 4 is a circuit diagram showing the flashlamp driver 122. Generally, the circuit has a simmer power supply 132 and a high voltage power supply 130 for two Xenon flashlamps, LP1 and LP2. As is known, the simmer supply 132 maintains the flashlamps LP1, LP2 at an operational temperature, so that when they are driven by the high voltage power supply, the light generation is virtually instantaneous. Two series capacitor banks, Cx, Cy, with parallel resistors Rx and Ry, respectively, are charged by the high voltage power supply to supplement the power provided to the flashlamps LP1, LP2 when pumping the alexandrite.

Conventionally, laser flashlamps are driven by the high voltage power supply through a passive pulse-forming network (PFN). The present invention replaces this analog-style network with two IGBT transistors Q1,Q2 in an active PFN configuration. In operation, these transistors are normally in a non-conducting state. This connects the flashlamps, LP1 and LP2, only across the simmer power supply 132. When an IGBT driver 134, however, is signaled to initiate the generation of the laser light pulse, trigger signals are sent to both transistors Q1, Q2. This connects the series connected Xenon flashlamps LP1,LP2 to ground through resistors R7 and R8 and across the high voltage power supply 130. The flashlamps then draw current from both the high voltage power supply and the series capacitor banks Cx and Cy.

The use of transistors Q1,Q2 to connect the flashlamps across the high voltage power supply 130 has a number of advantages relative to prior art passive PFN circuits. First, with a passive PFN, it is generally difficult to provide for selection of the pulse duration; passive pulse-forming networks are generally tuned only to generate a pulse of a single duration. In contrast, the trigger pulse provided to the IGBT transistors Q1,Q2 may be easily digitally controlled via the IGBT driver 134, allowing any desired pulse duration consistent with the laser's characteristics and power supply. This is illustrated by the pulse duration selector 135 that preferably enables the operator to select pulse durations of 5, 10, or 20 msec. The only limitation on the pulse is the current the transistors Q1 and Q2 can conduct before they begin to be damaged. This factor, however, does not provide a hard upper limit to the pulse duration generated by the network since two or more transistors may be connected in parallel to meet the electrical current demands.

Figure 5A:
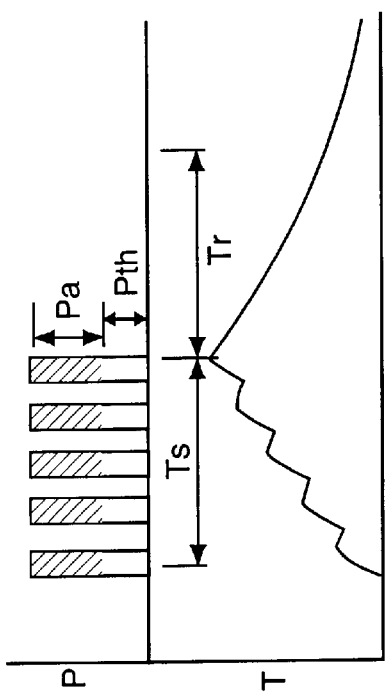
FIGS. 5A and 5B are plots of power/induced temperature as a function of time for pulse periodic heating and constant amplitude heating, respectively.

Further, the use of the active PFN additionally allows for the use of pulse periodic heating techniques. FIG. 5A is a plot of the power (P) supplied to the laser and the resulting temperature (T) of the targeted vessel as a function of time. A series of short subpulses are generated, with a fractional duty cycle over the selected effective pulse duration Ts by controlling transistors Q1 and Q2. Each subpulse has a duration of 1,2, or 3 msec.

Figure 5B:
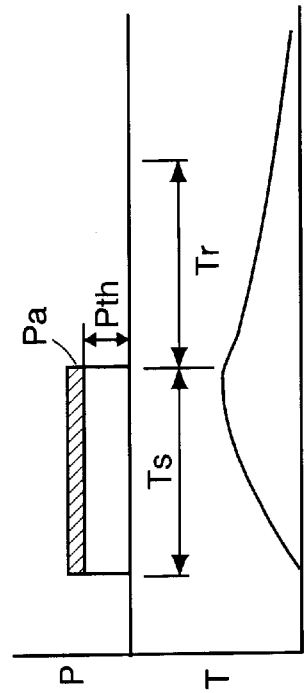

Pulse periodic heating techniques have certain advantages over constant amplitude heating shown in FIG. 5B, especially in flashlamp-excited lasers. A certain threshold of pump power Pth is needed to begin lasing in the gain media, the alexandrite. The excess flashlamp power Pa over this lasing threshold then determines the amplitude of the laser output beam. By compressing the generated light into a series of shorter pulses, a higher percentage of the pumping power used to excite the media is realized in the power of the output beam as shown by hatched regions in FIG. 5A. In contrast, as shown in FIG. 5B, when operating the laser in a constant amplitude mode, most of the power is consumed in reaching the lasing threshold. This power is lost to heat, increasing the need for liquid cooling and the demands on the power supply.

As also shown in FIGS. 5A and 5B, the temperature rise T induced in targeted hair producing structures by the pulse periodic heating is only slightly different than that induced by the continuous amplitude heating. The tissue temperature increases in a stepwise fashion with pulse periodic heating as opposed to gradually in the continuous amplitude case. This difference in heating, however, does not affect the efficacy of the therapy because it is only the maximum temperatures that determine whether or not the structures are destroyed.

With shorter pulse durations the advantages of pulse periodic heating techniques relative to constant amplitude heat become less pronounced. Generally, in the context of the inventive system, pulse periodic heat is only required for effective pulse durations of greater than 10 msec.

In the preferred embodiment, the duty cycle of the series of subpulses is less than 50%. Further efficiency gains are made when the duty cycle is dropped to 25% or lower. Ten or more subpulses is the series are generated across the selected effective pulse duration of 20 to 40 msec, or greater. In total, this series of subpulses carries the fluence needed to damage the hair structure, i.e., 10 and 50 J/cm$^2$.

Figure 6:
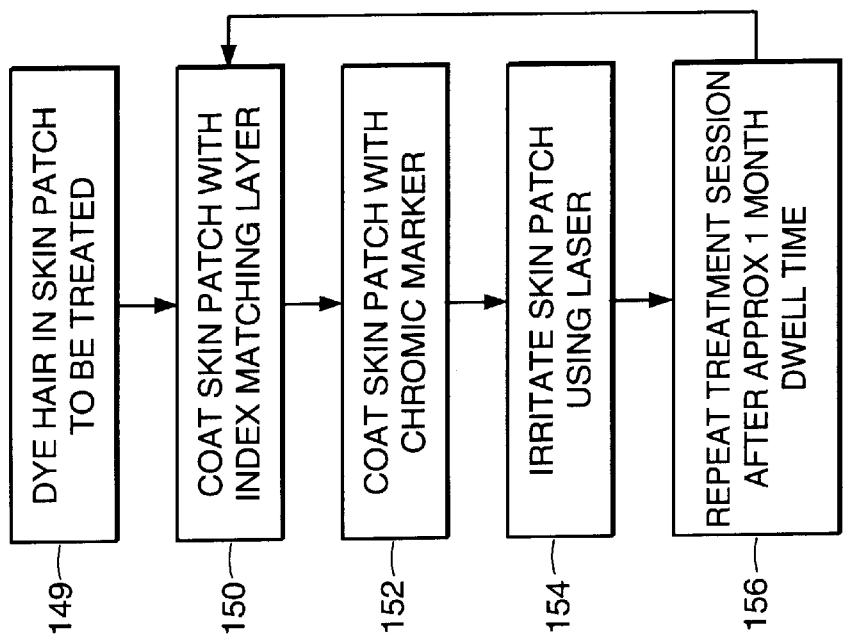
FIG. 6 is a process flow diagram showing hair removal according to the invention.

FIG. 6 is a method diagram showing the inventive hair removal technique using the alexandrite laser.

As a preliminary step 149, it may be helpful to have some patients first dye the hair in the skin patch to be treated. This is especially helpful for those patients having light-colored hair. The hair coloring is perform with any dark-colored commercially available hair dye. It is preferably performed by the patient in the days proceeding the laser treatment. As with these commercially hair dyes, the dyeing effect penetrates deeply into the hair shaft in the follicle to the papilla. This facilitates the absorption of the laser energy into the hair producing structures in the papilla and surrounding it, which increases selectivity.

The skin patch to be treated is first coated with the index-matching layer in step 150. The thermochromic or photochromic marker is also be coated over the skin patch in step 152 possibly with the index-matching layer.

The skin patch is then irradiated with the laser light pulse in step 154. The entire surface of the, skin patch is preferably irradiated with about 20 J/cm$^2$ using separate or slightly overlapping spots on the skin. The spots are located on the skin to ensure treatment of each follicle. The number of laser light pulses needed to irradiate the skin during each application depends upon the spot size, which depends on the laser's power. A higher powered laser can achieve the 20 J/cm$^2$ of energy necessary in the 5 msec pulse duration and thus can use a larger spot size. Seven millimeters spot size represents a good trade-off between laser power available under a current technology and a spot size that is large enough to efficiently treat the areas in a reasonably time. The thermochromic or photochromic marker indicates to the operator those parts of the skin that already have been treated.

Medical experiments have suggested that better results occur if the skin patch is irradiated only once in the same treatment session. Preferably, each section of the patch should receive one 5 msec laser light pulse providing a fluence of 20 J/cm$^2$.

This protocol then is repeated after approximately month long intervening dwell intervals in step 156. Generally, the first session is not entirely successful at removing all of the hair. Those follicles that do not contain a hair shaft generally are insufficiently irradiated to terminate any future hair growth. The absence of the added absorption of the hair shaft results in lower temperatures than that necessary to sufficiently damage the hair producing structures. During the first irradiation, most of the hair follicles that contain hair are destroyed. Then, across the intervening dwell interval, those follicles that previously did not have hairs grow their own hairs so that when treatment again is performed those hair follicles showing new growth are destroyed. For complete hair removal, this process generally must be repeated three or four times with the hair re-dyeing of step 149 repeated as necessary.

In the preferred embodiment, the effective pulse durations and fluence are selected using the principle of thermokinetic selectivity. Specifically, effective pulse durations of greater than the thermal relaxation times of the structures such as skin, which are to remain undamaged by the irradiation, and nearer to the relaxation times of the targeted structures, hair follicles, are used. This process is described in the attached appendix entitled "The Principle of Thermokinetic Selectivity," which is incorporated herein by this reference. Specifically, effective pulse durations of greater than 40 msec with fluences up to 30 J/cm$^2$ are implemented, preferably using pulse periodic heating principles.

While this invention has been particularly shown and described with references to preferred embodiments thereof, it will be understood by those skilled in the art that various changes in form and detail may be made therein without departing from the spirit and scope of the invention as defined by the appended claims.

THE PRINCIPLE OF THERMOKINETIC SELECTIVITY

1. Introduction

Epilation using lasers and incoherent light sources has become the subject of great discussion in the medical laser industry in the last five years. The first of these systems was the Softlight laser distributed by Thermolase. The Softlight system uses a Q-switched Nd:YAG laser at low fluences with an exogenous chromophore that absorbs 1.06 micron light. Although it has been on the market the longest, not much has been published about the mechanism of hair destruction using this system.

At the April 1995 meeting of the American Society of Laser Surgery and Medicine, Grossman (1) reported on a second approach for hair removal based on thermal destruction of hair follicles. This approach is better understood because of the publication of information by several different groups. The thermal effect lasers and other light sources for hair removal are based on the principle of Selective Photothermolysis (2), SP. However, it soon became apparent that Grossman's relatively short pulse laser was not optimum in preserving the epidermis of darker skin types. This led to a reexamination of SP and the derivation of a new principle called Thermokinetic Selectivity, TKS.

2. Pulse Duration Effect

2.1 Selective Photothermolysis

The fundamentals of Selective Photothermolysis, SP, were conceived by Rox Anderson. Ideas based on SP were discussed in internal seminars at the Wellman Laboratories of Photomedicine at the Massachusetts General Hospital, Boston, Mass., starting in the late seventies. These ideas were evaluated and tested clinically over the next few years. Anderson and Parrish first used the term, Selective Photothermolysis, in a publication in *Science in* 1993 (2).

This publication sparked great interest. The paper has been cited on numerous occasions since and will continue to be cited for years to come. The novelty was not in the choice of optimum wavelengths for light used in selective microsurgery. That concept of selectivity by choice of wavelength was well understood and explained by medical laser investigators such as by Ohshiro (3). The greater interest was in the use of pulsed lasers. SP showed that continuous wave, CW, lasers could induce unwanted collateral damage to structures adjacent to the target by heat conduction. With selective absorption, and use of pulsed lasers of adequate power, the light source could be turned off before a significant fraction of the heat generated in the target could diffuse to adjacent structures. The result was highly selective clinical endpoints. The concept, though simple, is still not well understood. Inappropriate terms such as "cold lasers" have been generated to sometimes explain the concept.

The paper did, however, popularize a property called "thermal relaxation time." The thermal relaxation time, $t_r$, is defined as the time required for the central temperature of a Gaussian temperature distribution with a width equal to the target's diameter (for cylindrical targets) to decrease by 50%. In a layperson's term it is a characteristic time required for a target to cool. This time depends on the target's size and shape.

This important parameter is now universally referenced in clinical experiments on laser/tissue interactions. The authors of the seminal paper make no claim as to the preciseness of this number and in subsequent papers claim it is relevant to only within an order of magnitude. But its usefulness in experimental design has been well established.

With the introduction of SP, clinicians have been instilled with the necessity of using pulsed lasers with an exposure time less than the thermal relaxation time of the target. Moreover, SP implied that the optimum pulse duration be equal to the thermal relaxation time of the target (4). That this should be so can not be justified on the basis of thermal diffusion. If the only concern is to limit thermal diffusion's contribution to non-specificity, then the shorter the pulse, the better. But, too short a pulse may result in high intensities that contribute adverse effects not related to thermal diffusion (4). Table 1 shows generally accepted rules as to how to choose pulse duration to promote specificity.

TABLE 1

Selective Photothermolysis

|  |  | Selectivity |
|---|---|---|
| Case I | $t_L < t_r$ (target) | + |
| Case II | $t_L \approx t_r$ (target) | + |
| Case III | $t_L > t_r$ (target) | − |

$t_L$ Pulse duration of the laser
$t_r$ (target) Thermal relaxation time of target The thermal relaxation time was defined by Anderson (2,3) to be, $$t_r = \frac{d^2}{gk}$$

where d is a characteristic dimension of the target such as the diameter of a sphere or cylinder or the thickness of a planar target, k is the thermal diffusivity and g, a geometric factor that is associated with the shape of the target. Table 2 gives the thermal relaxation times for different g and d.

TABLE 2

Thermal Relaxation Time
Examples of $t_r$

|  |  |  | $t_r$ (msec) |  |  |
|---|---|---|---|---|---|
| | $t_r$ | d | $100\mu$ | $200\mu$ | $300\mu$ |
| Planar | $d^2/4k$ | thickness | 19 | 76 | 131 |
| Cylindrical | $d^2/16k$ | diameter | 4.8 | 19.2 | 43.2 |
| Spherical | $d^2/27k$ | diameter | 2.8 | 11.2 | 25.2 |

$t_r = d^2/gk$
d = characteristic dimension
g = geometric factor
k = thermal conductivity The thermal relaxation time of a target is an important concept, but to use it alone to validate the complex kinetics involved in laser/tissue interaction leaves much to be desired. If SP is examined closely, the assumptions are completely theoretical and in fact, the analytic equations on which SP is based are not easily solved in practice in a useful manner.

Dierickx (5) in a paper published more than a decade after the publishing of the original SP articles attempts to resolve some of the issues raised by SP. She reports on experiments showing that there is little clinical difference in choosing initial temperature conditions from models that are intuitively acceptable (Gaussian spatial temperature distribution) or conceptually simple (Green's finction). She shows that either model is acceptable, but unfortunately the equation derived is only valid for cooling. It is difficult to get an analytical solution for the time resolved spatial temperature distribution in the target while the laser heating pulse is on.

The expression used by Dierickx (5), $$T(r,t) = \frac{1}{2kt}\int_0^\infty \left[\exp[-r^2 + (r^1)^2]/4kt\right]I_0\left(\frac{rr^1}{2kt}\right)g(r^1)dr^1 \quad (1)$$

can not be solved analytically during the heating cycle. With simplifying assumptions, an initial temperature distribution with a peak at the center of the cylindrical vessel can give a set of initial conditions, but the equation then only describes what happens as the target cools; a period of lesser interest in laser/tissue interaction.

It would be most desirable to get temporal and spatial temperature distribution while the laser pulse is heating the target, but this can only be done using numerical computations.

But even with numerical computations, the assumptions made must be examined scrupulously as will be seen in the case for modeling the epidermis.

In a publication, predating SP by a decade, Vassialiades (6) generates an expression for heating of a cylindrical target in cylindrical coordinates including thermal diffusion as, $$T(z, t) = \frac{Q}{2pc} \int_0^t \left(1 - e^{\frac{-d^2}{4k't}}\right) \text{erf}\left(\frac{z+1}{\sqrt{2kt'}} - \text{erf}\frac{z-1}{\sqrt{2kt'}}\right) dt \quad (2)$$

which can be solved analytically for targets with simple, cylindrical geometry. But even this expression is difficult to resolve. Given the lack of preciseness in stating the boundary conditions it may not be worth seeking a solution. It would be appealing to come up with simple expressions that can give an intuitive feel for the kinetics of the reaction and be correct to better than an order of magnitude.

2.2 ThermoKinetic Selectivity. Although it is not simple to get an exact analytical expression for temporal and spatial temperature distribution while the laser pulse is on, an approximate model can be derived from the observation of heating of materials in the presence of thermal conduction or convection. FIGS. 7A, B depicts a slab of a good thermal conductor being heated in the presence of cooling. The cooling can be done by convection to air or conduction to a transparent liquid in which the slab is immersed and heated by light. The slab absorbs heat and its temperature rises in a non-linear manner because of cooling. When the heat source is turned off, the slab cools with an exponential decay. Depending on the mass and geometry of the slab, the temperature can reach an asymtote if the heat is on long enough.

Figure 9A:
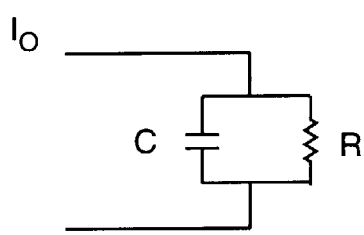
FIG. 9A is a circuit diagram illustrating a leaky capacitor being charged by a constant current source, $I_c$.

This heating model can be represented as a leaky capacitor being charged by a constant current source as given in FIG. 9A. The solution to this configuration is identical to the solution for a capacitor being charged by a constant voltage source through a series resistor, FIG. 9B.

Figure 9B:
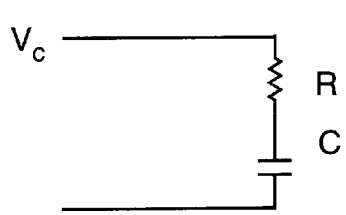
FIG. 9B is a circuit diagram illustrating a capacitor being charged by a constant voltage source, $V_c$, through a series resistor.

The equation in FIG. 9B is the traditional solution described in elementary electrical engineering. Its relation to time constants in tissue interaction is described in Reference 7a,b.

The temperature rise in tissue heated by laser radiation can be obtained using the following equation, $$\Delta T = \frac{\Delta E'}{mC_m} = \frac{\Delta E'}{\rho \Delta V C_m} \quad (4)$$

$\Delta E'$ = energy absorbed by mass $m$
$C_m$ = heat capacity of mass $m$
$m$ = mass of the heated volume $\Delta V$
$\rho$ = density of the volume $\Delta V$, typically taken to be the density of water
$\Delta V \propto d \times A'$    $A'$ is the projected area exposed to the light flux and $d$ a characteristic thickness of the volume $\Delta V$ Then $$\Delta T = \frac{\Delta E'}{\rho \Delta V C_m} \propto \frac{\Delta E'}{\rho d A'} \frac{1}{C_m}$$

The amount of heat generated is proportional to the light absorbed.

$$\Delta E' F(A')(1-e^{\alpha a})$$

where $\alpha$ = absorption coefficient and
$a$ = absorption depth, and
$F = \frac{E}{A}$ = Fluence irradiating the absorbing area $A$, $E$ is the energy in the laser pulse and $A$ the spot size Then $$\frac{\Delta E'}{A'} = F(1 - e^{-\infty}) = \frac{E}{A}(1 - e^{-\infty})$$

and now, $$\Delta T \propto F(1 - e^{-\infty}) \frac{1}{\rho d C_m}$$

A time dependence can now be included for a constant intensity laser source and using the derivation from FIG. 9B.

$$\Delta E(t) = \frac{F}{t_L} \times t$$

$$\Delta T(t) \propto \frac{Ft}{t_L}(1 - e^{-t/t_r})(1 - e^{-\alpha a})\left(\frac{1}{\rho d C_m}\right)$$

This equation is dimensionally proper but is not correct, because in the limit of $t_L \gg t_r$, the temperature rise is the same as the adiabatic, no heat loss case.

We can now compare this equation to the electric analog equation (3a).

$$V(t) = I_o R(1 - e^{t/tRC})$$

For the limiting case $t \to \infty$ $$V(t \to \infty) = I_c R = I_o \frac{t_{RC}}{C}$$

Where RC=$t_{RC}$

The constant current source $I_o$ is equivalent to the constant light source $F/t_L$, the capacitance C corresponds to the thickness of the absorber in the case of the light experiment and the time constants relate to each other identically.

$\Delta V \Rightarrow \Delta T$ $I_o \Rightarrow F/t_L$ $\frac{1}{C} \Rightarrow \frac{1}{\rho d C_m}$ $t_{RC} \Rightarrow t_r$ and by inspection and substitution, $$\Delta T(t) \propto \frac{t_r}{t_L} F\left(\frac{1}{\rho d C_m}\right)(1 - e^{-\alpha a})(1 - e^{-t/t_r}) \quad (5)$$

When, $$\frac{t_L}{t_r} \gg 1,$$

the final temperature rise is proportional to $$\frac{t_r}{t_L},$$

showing the lowering of the ultimate temperature by thermal conduction.

But when $$\frac{t_L}{t_r} \ll 1,$$

the term, $$\frac{t_r}{t_L}(1 - e^{-t_L/t_r})$$

gradually reaches unity and becomes the adiabatic case with no heat loss. At $t=t_L$, the final temperature rise can be expressed in terms of $t_L$ and $t_r$ as, $$\Delta T(t_L) \propto \frac{t_r}{t_L} F\left(\frac{1}{\rho d C_m}\right)(1 - e^{-a a})(1 - e^{-t_L/t_r}) \quad (6)$$

For simplicity, the approximation will now be replaced by the equality, and ρ is considered to be 1 and from hereafter the units are CGS. If the equation is to be used to obtain quantitative results and compared to experiments, the remittance R from the impinging beam must be included for completeness. Hence $$\Delta T(t_L) = F(1 - R)(1 - e^{-a a})\left(\frac{1}{d C_m}\right)\left(\frac{t_r}{t_L}\right)(1 - e^{-t_L/t_r}) \quad (7)$$

Figure 10:
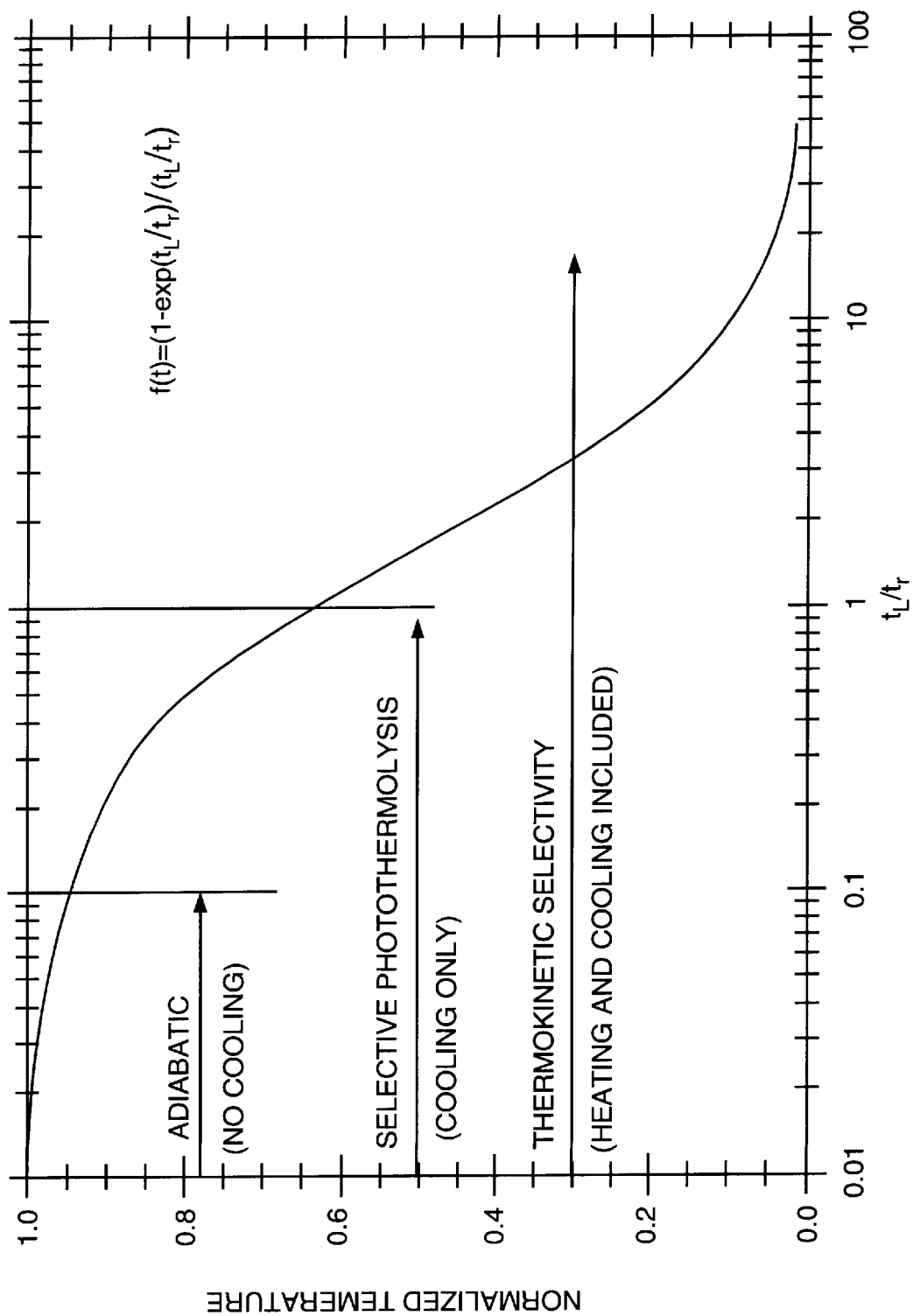
FIG. 10 is a graphical representation of the thermokinetic selectivity equation, in reduced units.

This equation is called the TKS equation is graphically represented in reduced units in FIG. 10. The figure shows the region of validity for SP. Most importantly, unlike SP, the equation can predict absolute temperatures given the necessary physical parameters. The ability to generate quantitative values for a set of boundary conditions is a great improvement over Selective Photothermolysis.

The rapid decrease in ultimate temperature at pulse durations greater than the thermal relaxation time allows for discrimination or selectivity based on the relation between $t_r$ and $t_L$. This is the basis for TKS and TKS can be exploited in many clinical applications.

Figure 11:
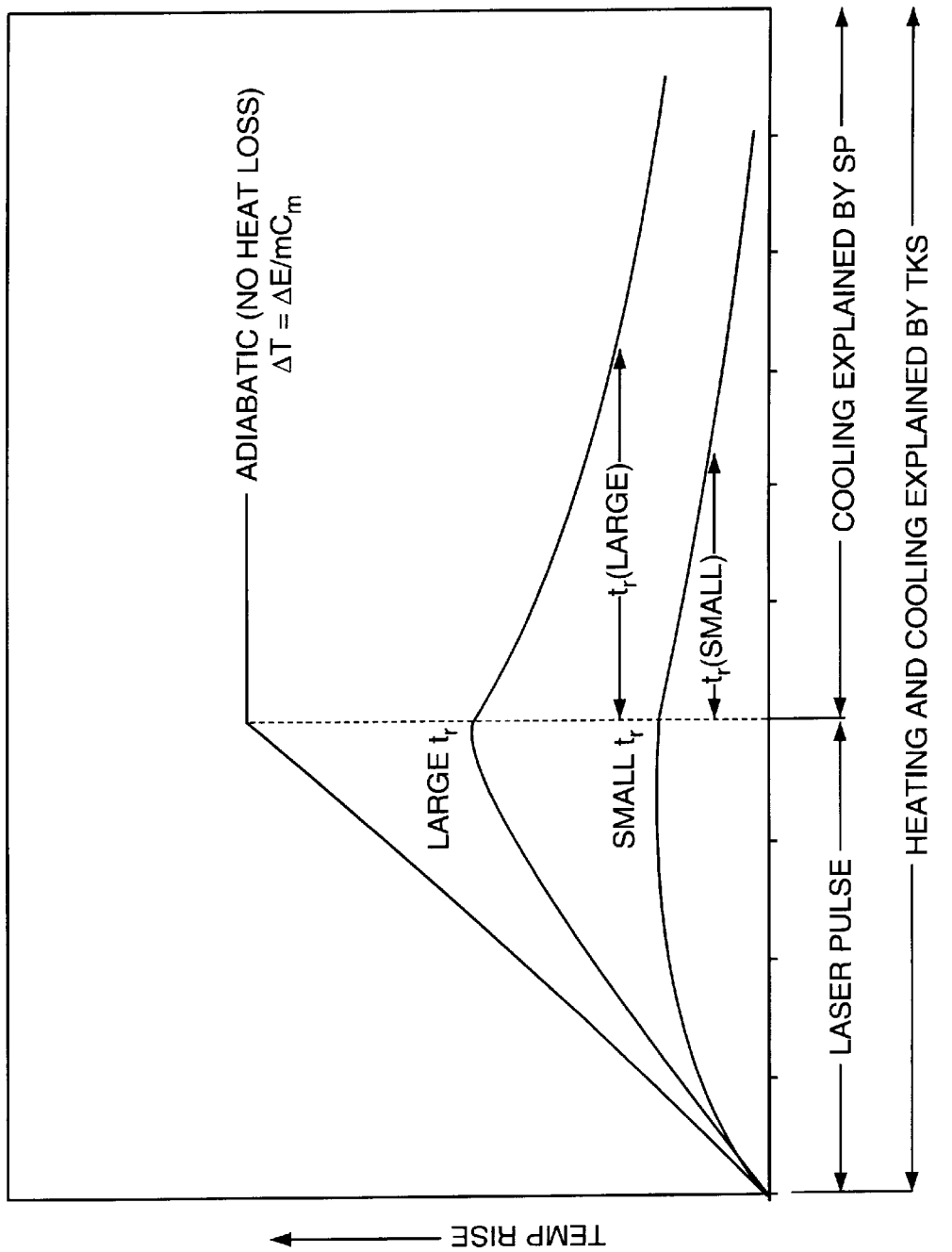
FIG. 11 is a plot of temperature rise versus time depicting the heating of targets with different thermal relaxation times, $t_r$, with a laser pulse of duration $t_l$.
Figure 12:
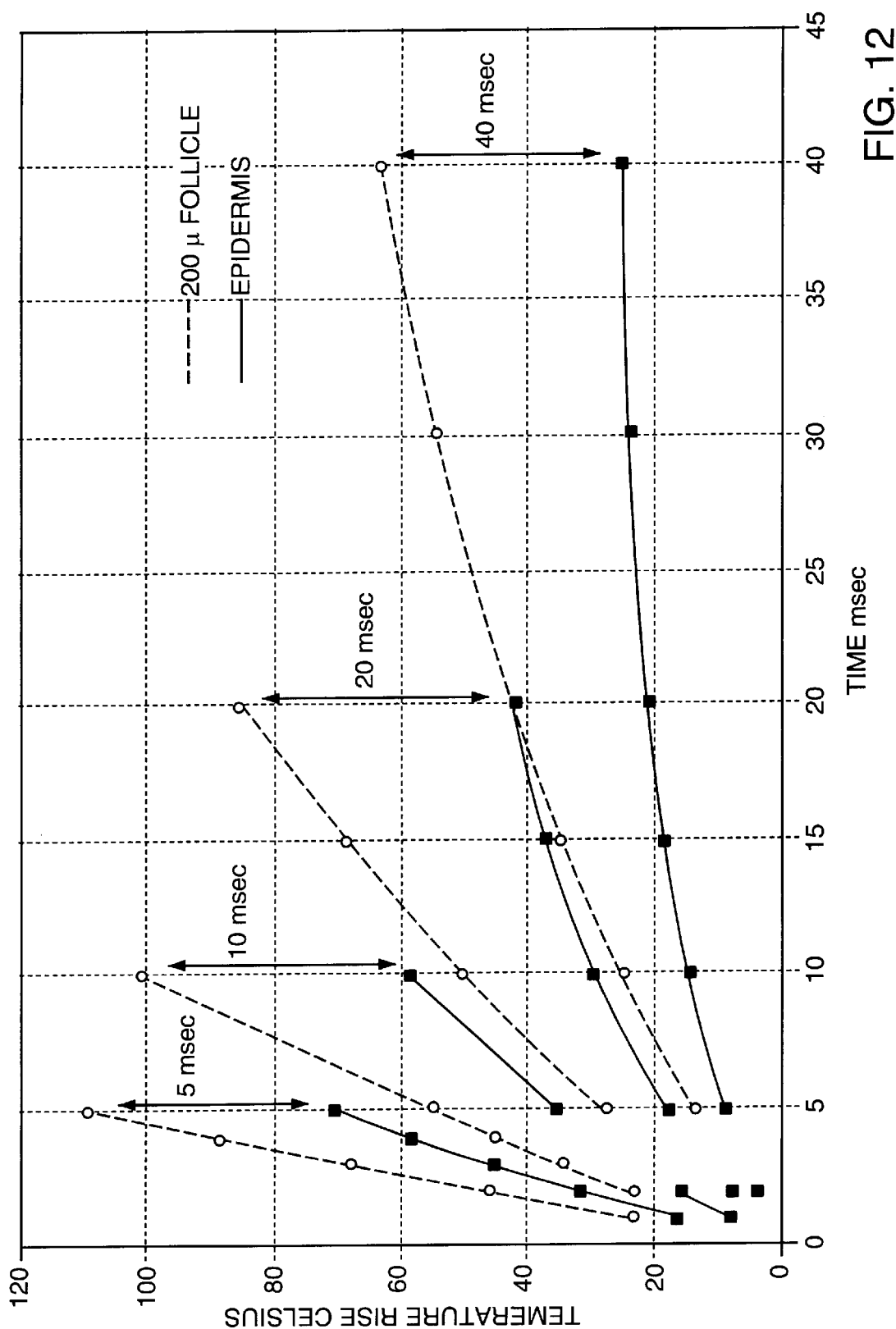
FIG. 12 is a plot of temperature rise versus pulse duration at a consistant fluence of 20 J/cm² for Asian skin, where the epidermis is damaged at a temperature rise of 38° C and the follicle is damaged at a temperature rise of greater than 67° C.

FIG. 11 depicts the heating of targets with a small $t_r$ and a large $t_r$ with a laser pulse of duration $t_L$. The laser pulse duration, $t_L$, as shown is longer than the shorter $t_r$, but less than or equal to the larger $t_r$. Our analytic model shows the temperature of the target rising linearly as is expected in the no cooling, adiabatic case when $t_L \ll t_r$. The pulse duration effect calculated by the TKS equation is applied to the epidermis and hair follicle and graphically depicted in FIG. 12.

Similarly, the temperature of a target with a large $t_r$ on the order of and greater than the heating pulse duration will continue to rise while a target with a small $t_r$ will eventually cool at the same rate it is being heated and the temperature reaches a maximum.

Discrimination or selectivity can be achieved by using the difference in $t_r$ and selecting heating pulse duration to attain the desired end temperature.

Table 1 can be extended to include selectivity based on TKS. The pulse duration conditions are bounded with a lower limit and an upper limit making TKS more precise than SP. The result is tabulated in Table 3.

TABLE 3

Selectivity vs. Thermal Relaxation Time

|  |  |  | Selectivity | Type |
|---|---|---|---|---|
|  | Case I | t(laser) < $t_r$ (target) | + | SP and TKS |
|  | Case II | t(laser) ≈ $t_r$ (target) | + | SP and TKS |
|  | Case III | t(laser) > $t_r$ (target) | − | SP and TKS |
| and, | Case IV | t(laser) < $t_r$ (target)<br>t(laser) ≫ $t_r$ (nontarget) | + | TKS |

Figure 13:
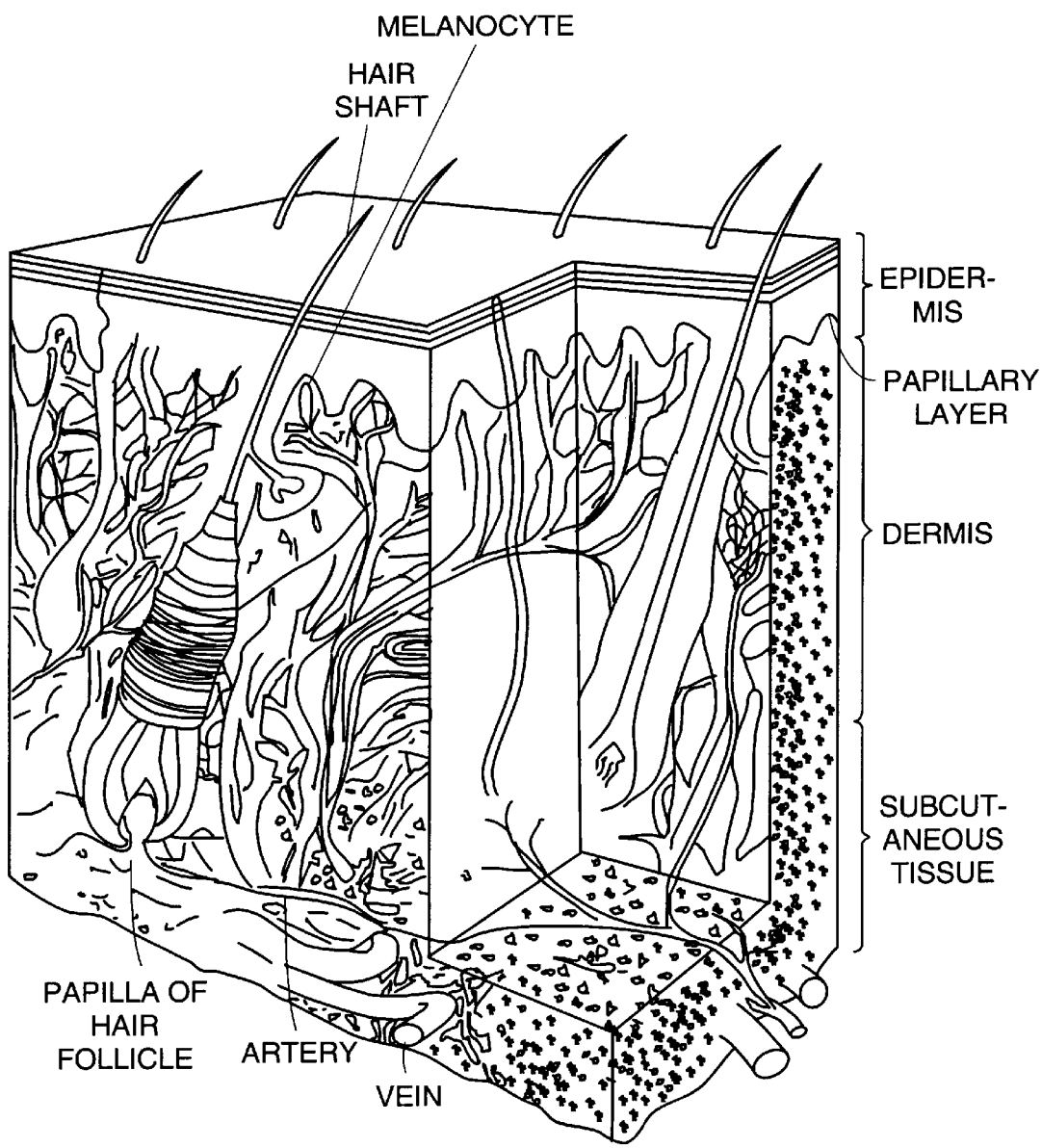
FIG. 13 is a cross-sectional view of the skin.

2.3 Thermal Relaxation Times. The thermal relaxation times for structures of simple geometry such as a planar layer, a cylinder or a sphere can be calculated using the equation $t_r = d^2/gk$. However, it is very difficult to calculate the absorption depth of the melanin layer in the epidermis because the melanosomes are not uniformly distributed throughout the epidermis. Furthermore, the melanin layer is adjacent to the papillary dermis, which is highly convoluted, FIG. 13 taken from Reference 10. The wrinkling exposes considerable surface area and the thermal relaxation time for a 100-micron epidermis is not the 20 msec as calculated for a planar layer but is much shorter.

Since the $t_r$ in TKS equation is analogous to the electric time constant t=RC, the $t_r$ of the epidermis is at the 1/e level and not the ½ temperatures used in standard SP discussions. The ½ temperature time constant is 0.693 as long as the 1/e time constant.

On the other hand, for the hair follicle, the geometry is simple and the thermal relaxation time $t_r = d^2/16k$ can be used when corrected by dividing by 0.693 for use in the TKS equation. For a 200-micron follicle, the $t_r$ is 19.2÷0.693=28 msec.

3. Application of the TKS Equation

First it is necessary to get an estimate of absorption of light in the epidermis. It is difficult to estimate the absorption in the epidermis as a function of wavelength. Published absorption spectra for Caucasian skin type (8) and Black skin type are available (9). We are not aware of similar absorption spectrum for Asian or similar skin types, but Ohshiro (10) shows reflection curves comparing Caucasian, Asian and Black skin types. In the near IR, the reflection of Asian skin lies midway between Black and Caucasian skin. Since reflection is a measure of absorption, the absorption of Asian skin can be inferred to lie midway between Caucasian and Black skin types. Hence a table of absorption by skin types can be constructed.

Figure 14:
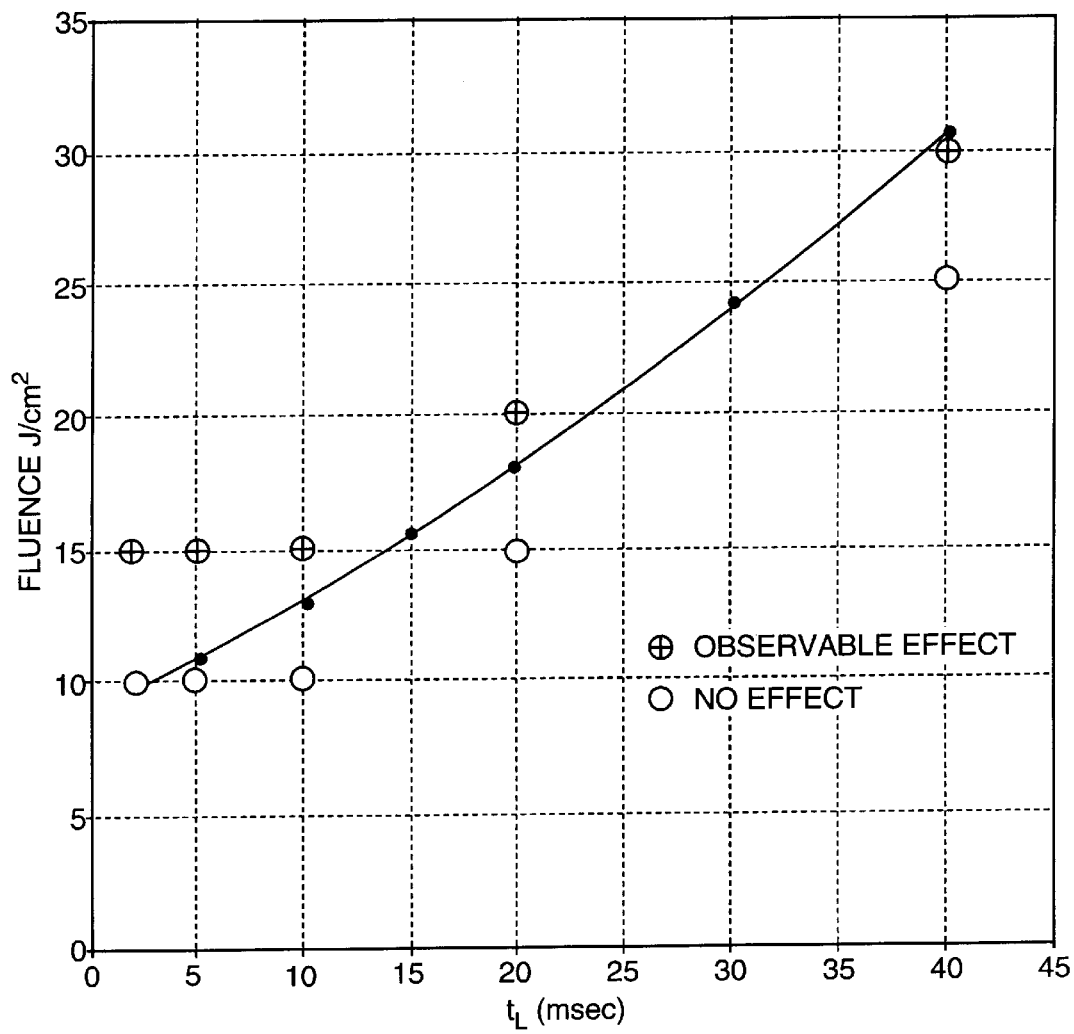
FIG. 14 is a plot illustrating the threshold fluence for observable epidermal effect versus laser pulse duration, $t_l$, at one hour post treatment, with the theoretical assumption that $\Delta T=38°$ C, $T=75°$ C, and $t_r=12$ msec.

To make the heat calculations, melanin is assumed to be dispersed in an absorbing layer 50 microns thick. The time constant for the epidermis is not that of a planar layer 100 microns thick but is shorter. An estimate of the thermal relaxation time of the epidermis was obtained from clinical experiments, FIG. 14, and found to be 12 msec. Fluences were increased in steps of 5 J/cm² at selected pulse durations. Finer steps will result in a better measure. It should be pointed out that the precision obtained here cannot be approached with the use of SP principles which claim a precision to an order of magnitude.

A table of absorption by skin types can now be constructed.

TABLE 4

Absorption by Different Skin types

| | | Absorption Coefficient (cm$^{-1}$) | |
|---|---|---|---|
| Skin Type | Reference | 694 nm | 755 nm |
| Black | (8) | 250 | 150 |
| Intermediate | (Interpolation) | 149 | 89 |
| Caucasian | (9) | 47 | 28 |

| | Fractional Absorption by 50 micron melanin layer in the epidermis | |
|---|---|---|
| Black | .71 | .53 |
| Intermediate (Asian) | .53 | .36 |
| Caucasian | .21 | .13 |

Light is lost by diffuse reflection. Diffuse reflection coefficients vs. wavelength for different skin types are tabulated by Svasaand (11). Light that is not absorbed by the epidermis or blood is used to heat the hair follicle. If scattering is assumed to be the same for the two wavelengths and thermal diffusion is neglected, the Alexandrite laser will heat the Asian epidermis 60% less than a ruby laser, and 36% more Alexandrite laser light than ruby laser light will reach the hair follicle at the same fluence. The superiority of the Alexandrite laser over the ruby laser for intermediate skin types such as in Asians is very pronounced.

The TKS equation (7) is repeated.

$$\Delta T(t_L) = F(1-R)(1-e^{\alpha a})\left(\frac{1}{dC_m}\right)\left(\frac{t_r}{t_L}\right)(1-e^{-t_L/t_r}) \quad (7)$$

For the epidermis, $$\Delta T = F(1-R)(Ae)\left(\frac{1}{d_e C_m}\right)\left(\frac{t_r}{t_L}\right)(1-e^{-t_L/t_r}) \quad (8)$$

where
 $\Delta T$=heat rise in the epidermis
 $A_e$=Absorption of incident light by epidermis
 $d_e$=thickness of the epidermis
 F=incident fluence
 R=diffuse reflection or remittance
 $t_r$=thermal relaxation time of the epidermis
 $t_L$=laser pulse duration
For the hair follicle, $$\Delta T_f = F\left(\frac{F_x}{F_i}\right)(A_f)\left(\frac{1}{d_f C_m}\right)\left(\frac{t_r}{t_L}\right)(1-e^{t_L/t_r}) \quad (9)$$

Selected Example for Study
 Intermediate (Asian) Skin with Dark hair

| | 755 nm |
|---|---|
| Epidermis Absorption (Ref 8, 9, 10) | .36 |
| Remittance (Ref 12) | .50 |
| $d_e$ for epidermis | .01 cm |
| $d_f$ for follicle | .02 cm, .03 cm |
| $t_r$ for epidermis | 12 msec |
| $t_r$ for follicle | 28 msec (200$\mu$), 62 msec (300 $\mu$) |
| ($F_x/F_i$) normalized fluence at the follicle at 3 mm (Ref 13) | .5 |

Figure 15:
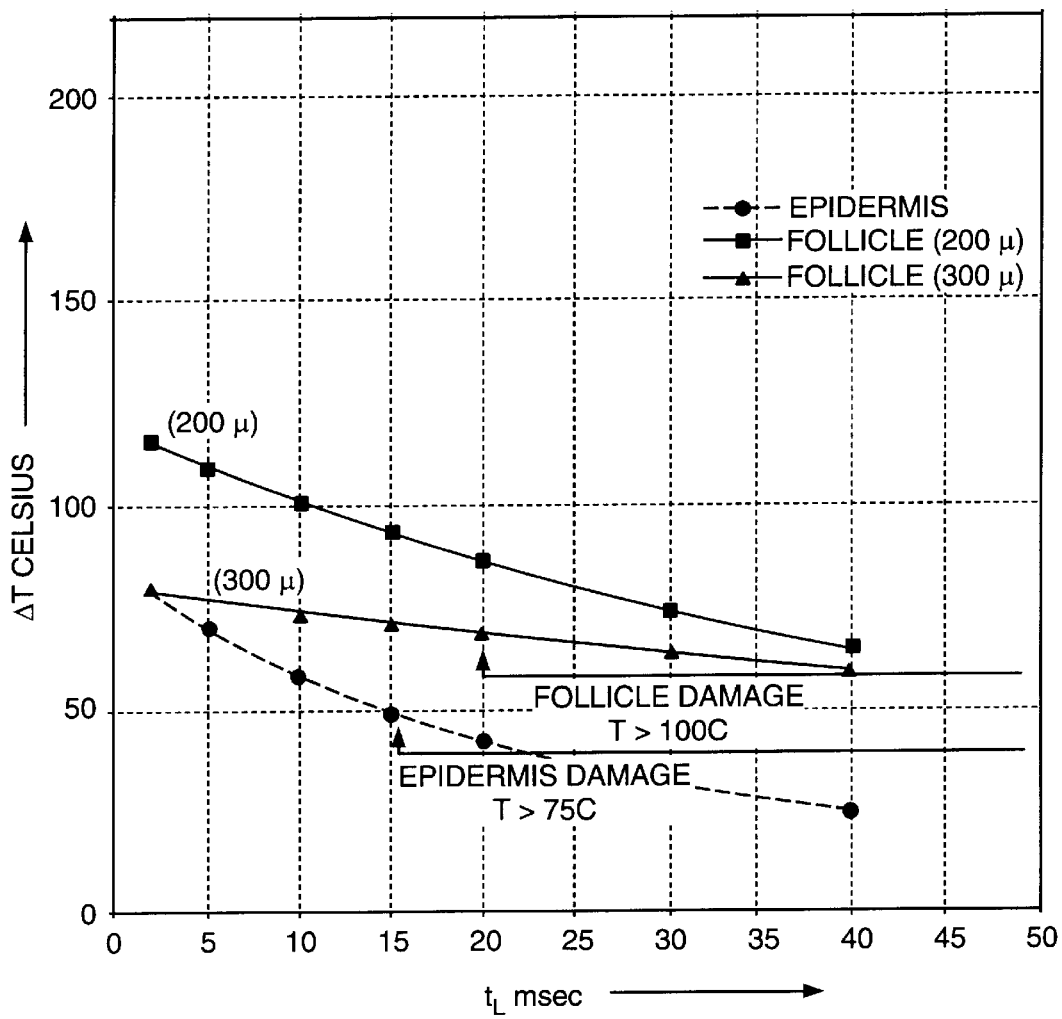
FIG. 15 is a plot of temperature rise versus pulse duration for Asian skin and dark hair at 20 J/cm², wher the Epidermis $t_r=12$ msec, Follicle (200 $\mu$) $t_r=29$ msec; and Follicle (300 $\mu$) $t_r=62$ msec.
Figure 16:
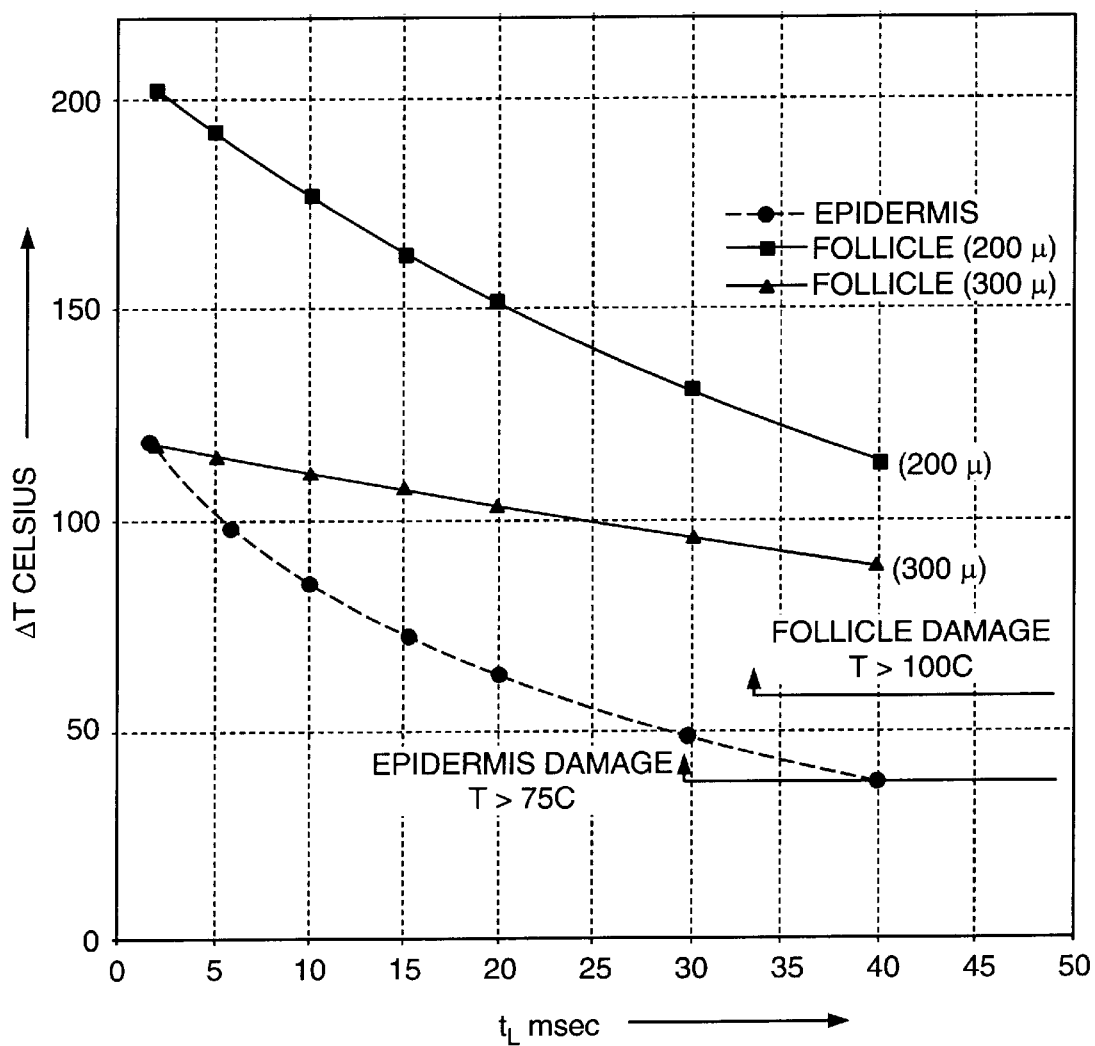
FIG. 16 is a plot of temperature rise versus pulse duration for Asian skin and dark hair at 30 J/cm², where Epidermis $t_r=12$ msec, Follicle (200 $\mu$) $t_r=29$ msec; amd Follicle (300 $\mu$) $t_r=62$ msec.

The TKS equation can be used to plot temperature rise for the epidermis and the hair follicle for the example given here. The results for two different fluences versus $t_L$ are plotted in FIGS. 15 and 16. Two different size hair follicles are used in the example to show the effect of TKS.

At a fluence of 20 J/cm$^2$ and a pulse duration of 20 msec, the epidermis is at damage threshold for Asian skin. This conclusion is verified by the clinical results in Japan. The follicle is expected to be damaged with a temperature rise of greater than 63 C. The larger follicle is just above damage threshold at this fluence. This operating point is workable, but may be too low for larger diameter hair follicles or those whose bulb may be down deeper than 3 mm.

According to TKS, fluences can be increased if the pulse duration is increased. At 40 msec, fluences up to 30 J/cm$^2$ can be used, FIG. 14. At 30 J/cm$^2$ at 40 msec, the epidermis is still preserved but the 200 micron follicle is heated 75 C higher than at 20 J/cm$^2$ at 20 msec. The higher fluences available at 40 msec can also heat smaller and or lighter hair to denaturation and consequently be more efficacious while still preserving the epidermis. Hence, 40 msec pulses are recommended for more effective hair removal.

REFERENCES

1. Grossman, M. C., Dierickx C., Farinelli W., Flottes T., Anderson R. R., Damage to Hair Follicles by Normal Mode Ruby Pulses, Journal of American Academy of Dermatology, 35, 889–894 (1996)
2. Anderson R. R., and Parrish J. A., Selective Photothermolysis: Precise Microsurgery by Selective Absorption of Pulsed Radiation, Science 220, 524–527, (1983)
3. Ohshiro, T., Laser Treatment for Nevi, Publisher, Medical Laser Research Co., 1980, p. 29.
4. Parrish J. A., Anderson R. R., Harrist T., Paul B., Murphy G., Selective Thermal Effects with Pulsed Irradiation from Lasers: From Organ to Organelle, J. Of Investigative Dermatology 80; 75–80 (1983) FIG. 2
5. Dierickx, C. C., Casparian, J. M., Venugopalon, V., Farinelli, W. A., Anderson, R. R., Thermal Relaxation of Port Wine Stain Vessels Probed in Vivo: The Need for 1–10 Millisecond Laser Pulse Treatment, Journal of Investigative Dermatology, 105, 709–714, (1995)
6. Vassiliadis, A., Ocular Damage from Laser Radiation in Laser Applications in Medicine and Biology V1, ed. Wolbarscht M. L. Plenum Press New York-London, 1971.
7a. Van Gemert M. S. C. and Welch A. J., Time Constants in thermal Laser Medicine, Lasers in Surgery and Medicine, 9, 405–421 (1989)
7b. Van Gemert M. J. C., and Welch, A. J., Approximate Solutions for Heat Conduction: Time Constant In Optical-thermal Response of Laser-irradiated Tissue, ed. A. J. Welch and M. J. C. Van Gemert, Plenum Press, New York-London, 1995, Chapter 13.
8. Anderson, R. R., Levins, P. C., Grevelink, J. M., Lasers in Dermatology, ed. by Fitzpatrick et al, Dermatology in General Medicine, 4$^{th}$ ed. McGraw Hill, NY, 1993.
9. Endoscopic Laser Surgery Handbook, p101, ed., Shapshay. Marcel Dekker 1987.
10. Ohshiro, T., Laser Treatment for Nevi, Publisher, Medical Laser Research Co., 1980, p. 42.

11. Svasaand, L. O., Norvang L. T., Fiskerstrand E. J., Stopps, E. K. S., Berns M. W., Nelson J. S., Tissue Parameters Determining the Visceral Appearance of Normal Skin and Port Wine Stains. Lasers in Medical Science 10, 55–65, (1995)
12. Jacques, S., Role of tissue optics and pulse duration on tissue effects during high power laser irradiation, Applied Optics, 32, 2447–2454 (1993), FIG. 1.
13. Svassand, L. O., Private Communication (1998).

What is claimed is:

1. A hair removal laser system, comprising:

a long pulse alexandrite laser which generates a laser light pulse having a duration greater than 10 msec, having a fluence between 10 and 50 J/cm$^2$, and being comprised of a series of subpulses over its duration; and a light delivery system which transmits the laser light output pulse to a hair-bearing skin of a patient.

2. The system as described in claim 1, wherein the effective pulse durations and fluence promote thermokinetic selectivity.

* * * * *